United States Patent [19]

Golden

[11] Patent Number: 4,755,170
[45] Date of Patent: Jul. 5, 1988

[54] VENIPUNCTURE AND CUTANEOUS SEALING DEVICE AND METHOD

[76] Inventor: Theodore A. Golden, 762 Wooddale Rd., Birmingham, Mich. 48010

[21] Appl. No.: 937,278

[22] Filed: Dec. 3, 1986

[51] Int. Cl.$^4$ .............................................. A61M 5/00
[52] U.S. Cl. ..................................... 604/52; 604/110; 604/192; 604/198; 604/263
[58] Field of Search ...................................... 604/51–52, 604/110, 117, 180, 192, 197, 198, 263; 128/325

[56] References Cited

U.S. PATENT DOCUMENTS

| | | | |
|---|---|---|---|
| 3,055,361 | 9/1962 | Ballard | 604/162 |
| 3,354,881 | 11/1967 | Bloch | 604/198 |
| 3,490,448 | 1/1970 | Grubb | 604/51 X |
| 3,606,889 | 9/1971 | Arblaster | 604/171 |
| 4,040,427 | 8/1977 | Winnie | 604/180 |
| 4,675,006 | 6/1987 | Hrushesky | 604/180 |

FOREIGN PATENT DOCUMENTS 2522973  9/1983  France ................................ 604/180

OTHER PUBLICATIONS

Dental Digest–Jun. 1944, p. 259.

*Primary Examiner*—Dalton L. Truluck
*Attorney, Agent, or Firm*—Cullen, Sloman, Cantor, Grauer, Scott & Rutherford

[57] ABSTRACT

A venipuncture and cutaneous sealing device and method which permits the capturing of a needle along its length either before or after a venipuncture, the engaging of the venipuncture site, and the sealing of both the puncture site and the needle tip. The sealing device may include two separable parts which are positioned along the length of the needle prior to the venipuncture. A split is provided in the sealing device to permit this capturing of the needle along its length or the sealing device may be pre-mounted on the needle along its length. The sealing device is slid or pressed into engagement with the skin at the venipuncture site and the needle is then withdrawn from the puncture site thereby leaving one part of the sealing device on the puncture site to seal the puncture site and absorb any blood at the site. Further, the other part of the sealing device is left on the needle to seal the tip of the needle and absorb any blood on the needle. The venipuncture and cutaneous sealing device prevents or substantially minimizes the possibility of patient blood coming into contact with the nurse, doctor or technician who is extracting blood from the patient. The sealing device may include a cover or shield which provides an additional barrier between the doctor, nurse or technician who is extracting blood and the absorbed blood within the sealing device.

28 Claims, 3 Drawing Sheets

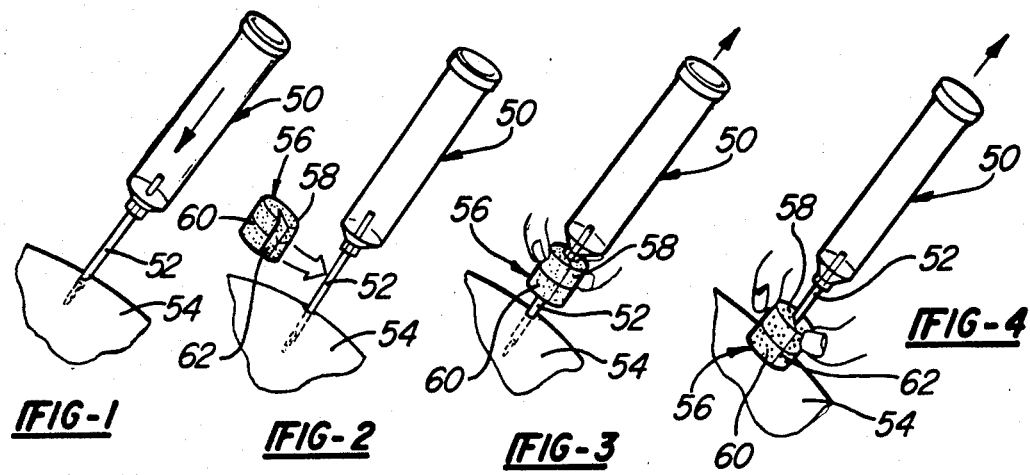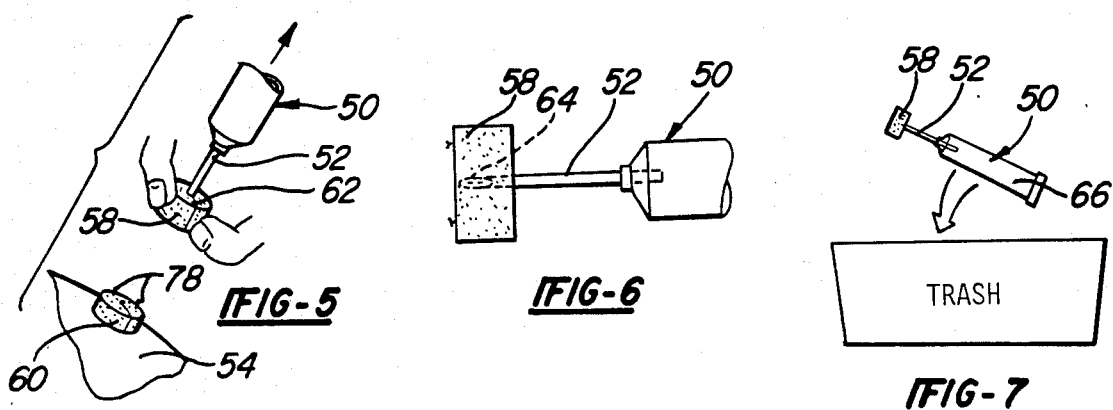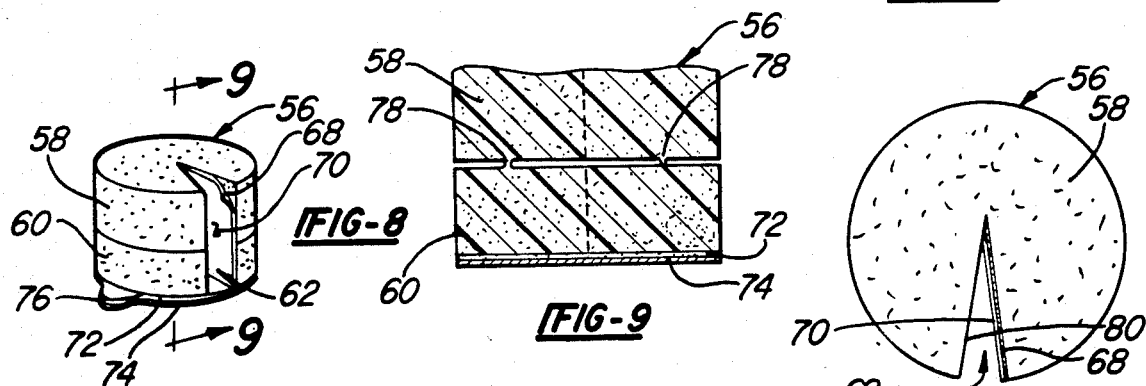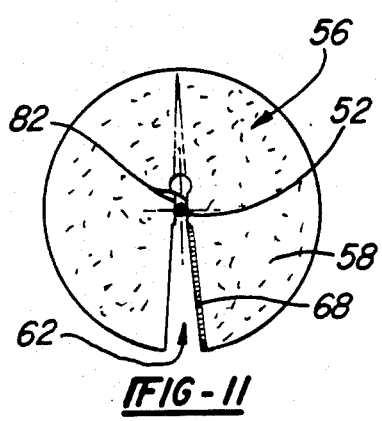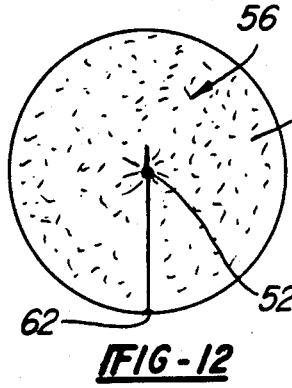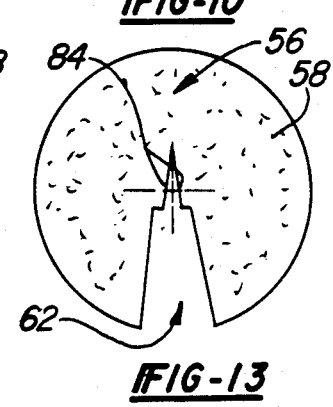

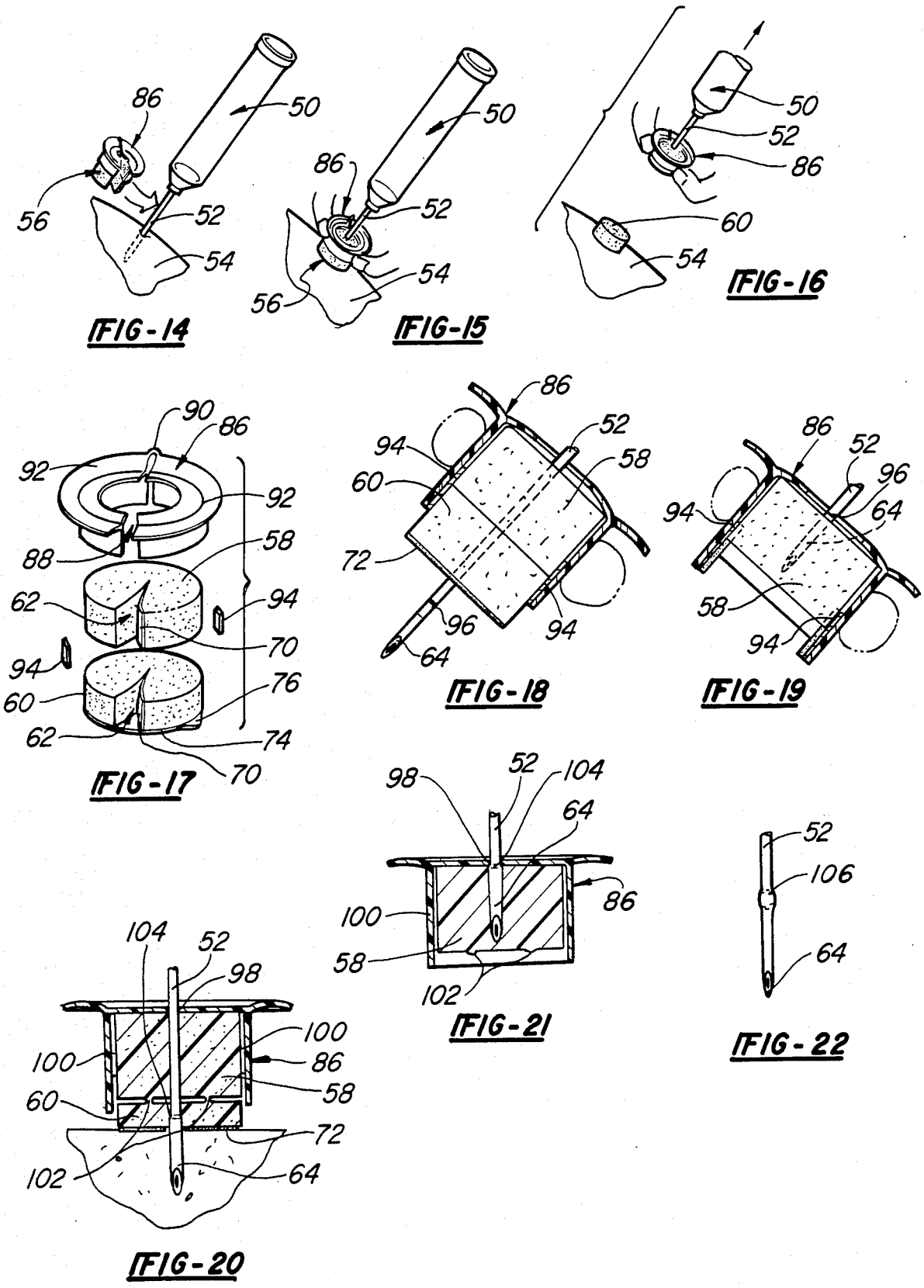

VENIPUNCTURE AND CUTANEOUS SEALING DEVICE AND METHOD

BACKGROUND OF THE INVENTION

The present invention relates to a venipuncture and cutaneous sealing device and method which permits the capturing of a needle either before or after a venipuncture, the engaging of the venipuncture site, and the sealing of both the puncture site and the needle tip.

It is a conventional to use needle devices for extracting blood for testing purposes. For example, in a conventional hypodermic syringe, the needle is inserted into a vein and a plunger is pulled or retracted to create a vacuum inside the syringe that causes blood to flow through the needle and into the body of the syringe. After the blood is received within the hypodermic device, the device is withdrawn which normally results in blood spurting out of the venipuncture site onto the surface of the puncture site and also some blood remaining on the outer surface of the needle. This also occurs with all other needle devices that are presently used for withdrawing blood or for intravenous medication.

There is a great concern today regarding the possibility that a patient's blood may come into contact with the nurse, doctor or technician who is extracting blood from that patient. Moreover, the possibility of blood coming into contact with anyone or anything else is of great concern in view of the possibility that serious and even deadly diseases may be transmitted. Thus, it is the principal object of the present invention to prevent or substantially minimize the possibility of patient blood coming into contact with the nurse, doctor or technician who is extracting blood from that patient. Further, it is an object of the present invention to prevent or minimize the possibility of blood coming into contact with anyone or anything else.

SUMMARY OF THE INVENTION

In accordance with the present invention, a venipuncture and cutaneous sealing device is disclosed to both seal the puncture site and needle tip, thereby preventing or minimizing the possibility of blood coming into contact with anyone else. In a preferred form, the sealing device includes two separable parts which capture the needle along its length prior to or after the venipuncture. A split is provided in the sealing device to permit this capturing or the sealing device may be pre-mounted on the needle. After the needle is used to make the venipuncture, the sealing device is slid or pressed into engagement with the skin at the puncture site. The needle is then withdrawn from the puncture site leaving one part of the sealing device on the puncture site to seal the puncture site and absorb any blood at the site. Further, the other separable part is left on the needle to seal the tip of the needle and absorb any blood on the needle. Thereafter, the needle device may be thrown into a receptacle for disposal.

As will be appreciated, the venipuncture and cutaneous sealing device of the present invention prevents or substantially minimizes the possibility of patient blood coming into contact with the nurse, doctor or technician who is extracting blood from the patient. The sealing device is made of a material that is absorbant, is sufficiently structural to permit separation, and may be self-sealing. If the material of the device does not already have adhesive in it, one or more surfaces of the split in the device may be coated with adhesive except at the area which surrounds the needle. A strippable cover may be used to cover the adhesive until it desired to capture the needle as previously described. An adhesive surface with a strippable cover may also be provided on the surface of the sealing part that contacts the skin at the site of the puncture. Further, a tab may be provided to assist in the stripping of that part away from the skin for disposal after sufficient clotting has occurred.

Frangible connectors are provided to permit the separation of the sealing device parts when the needle is withdrawn from the puncture. These connectors may be made of the same material used for the separable parts or other materials such as thread and the like.

Various configurations for the split in the sealing device may be utilized. For example, the split may simply be pie-shaped with adhesive on one or both sides of the opening that secures the sides together when the split is squeezed around the needle. Alternatively, other compression generating configurations may be provided for insuring compression of the material making up the sealing device around the needle. A tightly sealed compression fit is desired, however, to provide the desired sealing and absorption characteristics as the needle is moved into and out of the puncture site.

The sealing device may also include a cover or shield. The shield may include a separation or split matching the split in the sealing device with a flexible connection between the shield halves to permit the halves to close around the sealing device when squeezing pressure is applied to the outside of the shield. Moreover, an indicator mark may be provided on the needle to establish the amount of withdrawal of the needle to insure encapsulation of the needle tip within the sealing device. The shield provides an additional barrier between the doctor, nurse or technician who is extracting blood and the absorbed blood within the sealing device and the needle. Further, the shield may also provide for easier manipulation of the sealing device for smaller needles.

The sealing device may also be pre-mounted on the needle so that the doctor, nurse or technician does not have to perform the previously described capturing step of the needle prior to usage. A particularly convenient configuration for the pre-mounted sealing device includes a shield having an elongated resilient body portion with an inwardly directly end portion. Initially, the shield and sealing device are positioned at the base of the needle and after the venipuncture is made, the shield is pushed downwardly for causing the sealing device to contact the outer skin area around the puncture site. The needle is then withdrawn which detaches and separates the sealing parts and the shield is slid along the body of the needle device until the inwardly directed end portion of the shield snaps into engagement with a complementary circumferential recess in the needle device. This automatically results in the encapsulation of the needle tip at the correct position within the sealing device thereby eliminating the need to visually watch for a mark on the needle and also to insure the proper sealing position of the needle tip within the sealing device.

Other advantages of and meritorious features of the present invention will be more fully understood from the detailed description of the invention, the appended claims and the drawings, which are briefly described hereinbelow.

DESCRIPTION OF THE DRAWINGS

FIG. 1 is a perspective side view of a hypodermic device having a needle which has been inserted into a body area.

FIG. 2 is a perspective side view of the hypodermic device illustrating the venipuncture and cutaneous sealing device of the present invention.

FIG. 3 is a perspective side view illustrating the capturing of the needle by the sealing device of the present invention.

FIG. 4 is a perspective side view illustrating the sealing device being pressed into contact with the skin at the venipuncture site.

FIG. 5 is a perspective side view illustrating the withdrawal of the needle from the puncture site which leaves a part of the sealing device on the puncture site and a part of the sealing device on the needle.

FIG. 6 is a side elevational view illustrating the part of the sealing device that is left on the needle to seal the tip of the needle.

FIG. 7 is a side elevational view illustrating disposal of the sealed hypodermic device.

FIG. 8 is a perspective view of the venipuncture and cutaneous sealing device of the present invention.

FIG. 9 is a cross-sectional view taken along line 9—9 in FIG. 8.

FIG. 10 is a top plan view of the sealing device of the present invention.

FIG. 11 is a top plan view of the sealing device illustrating a different configuration for the split in the sealing device.

FIG. 12 is a top plan view of the sealing device illustrating capturing of the needle.

FIG. 13 is a top plan view of the sealing device illustrating yet another configuration of the split in the sealing device.

FIG. 14 is a perspective side view illustrating the sealing device of the present invention including a cover or shield.

FIG. 15 is a perspective side view illustrating capturing of the needle and movement of the sealing device into contact with the skin surrounding the puncture site.

FIG. 16 is a perspective side view illustrating separation of the parts of the sealing device of the present invention.

FIG. 17 is a perspective assembly view of the venipuncture and cutaneous sealing device of the present invention including a cover or shield.

FIG. 18 is a side elevational view, partly in cross-section, of the sealing device illustrated in FIG. 17.

FIG. 19 is a side elevational view, partly in cross-section, of the sealing device of FIG. 18 illustrating separation of the parts of the sealing device and sealing of the needle tip therein.

FIG. 20 is a side elevational view, partly in cross-section, of the sealing device illustrating the frangible connectors between the parts of the sealing device and the means for accurately positioning the needle tip within the sealing device upon withdrawal.

FIG. 21 is a side elevational view, partly in cross-section, illustrating the needle tip withdrawn into the sealing device.

FIG. 22 is a side elevational view of a needle having an enlarged portion for the purpose of permitting accurate positioning of the needle tip within the sealing device.

DETAILED DESCRIPTION OF THE INVENTION

Figure 23:
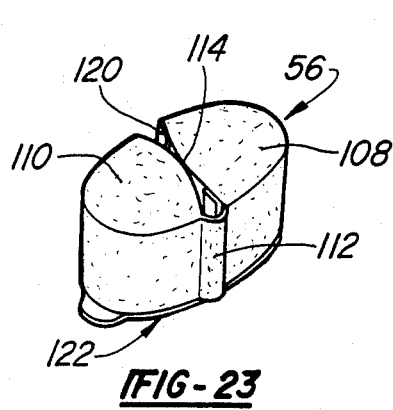
FIG. 23 is a perspective view of another configuration of the venipuncture and cutaneous sealing device of the present invention.

FIGS. 1-7 illustrate the venipuncture and cutaneous sealing device and method in accordance with the teachings of the present invention. The present device permits the capturing of a hypodermic needle either before or after a venipuncture, the engaging of the venipuncture site, and the sealing of both the puncture site and needle tip.

FIG. 1 illustrates a conventional hypodermic device 50 having a needle 52 which has been inserted into a body area, such as an arm 54, to puncture a vein. After blood is received within the hypodermic device 50, the device is withdrawn which would normally result in blood spurting out of the venipuncture site onto the surface of the puncture site and also some blood remaining on the outer surface of the needle 52. In accordance with the present invention, a venipuncture and cutaneous sealing device 56 is utilized to both seal the puncture site and needle tip as will be described.

Referring now to FIGS. 2 and 3, a sealing device 56, including two separable parts 58 and 60, is used to capture needle 52 along its length. A split 62 is provided in device 56 to permit this capturing of the needle. After capturing needle 52, device 56 is slid or pressed into engagement with the skin at the venipuncture site as shown in FIG. 4. Needle 52 is then withdrawn from the puncture site, thereby leaving part 60 on the puncture site to seal the puncture site and absorb any blood at the site as shown in FIG. 5. Further, part 58 is left on needle 52 to seal the tip 64 of needle 52 and absorb any blood on needle 52, as shown in FIGS. 5 and 6. Thereafter, the hypodermic device may be thrown into a receptacle 66 for disposal.

As will now be appreciated, the venipuncture and cutaneous sealing device 56 of the present invention prevents or substantially minimizes the possibility of patient blood coming into contact with the nurse, doctor or technician who is extracting blood from that patient. Moreover, sealing device 56 prevents or minimizes the possibility of blood coming into contact with anyone else since any blood on the needle tip is absorbed by and sealed within the part 58 of sealing device 56 that remains on the needle tip 64.

Referring now to FIGS. 8–13, sealing device 56 will be described in more detail. Device 56 is made of a material that is absorbent, is sufficiently structural to permit separation, and may be self-sealing. If the material of device 56 does not already have adhesive in it, one surface of split 62 may be coated with adhesive 68 as shown in FIGS. 8, 10 and 11, except at the area which will surround the needle 52. A strippable cover 70 is used to cover the adhesive 68 until it is desired to capture needle 52, as described above. No adhesive is provided at the area surrounding the needle so that the needle can freely move during puncture and withdrawal. An adhesive surface 72 with a strippable cover 74 may also be provided on the surface of part 60 that contacts the skin at the site of the venipuncture. Further, a tab 76, as shown in FIG. 8, may be provided to assist in the stripping of part 60 away from the skin for disposal after sufficient clotting has occurred.

An example of the means for permitting separation of parts 58 and 60 is illustrated in FIG. 9. Frangible connectors 78 are provided to permit the separation of part 58 from part 60 when needle 52 is withdrawn from the puncture. These connectors 78 may be made of the same material used for parts 58 and 60, or other materials such as thread and the like may be utilized.

Referring to FIGS. 10–13, various configurations for split 62 are illustrated. Split 62 may simply be pie-shaped as shown in FIG. 10 with adhesive 68 on one or both sides that contacts and secures the sides 80 together when the split 62 is squeezed around needle 52. Alternatively, compression generating configurations may be provided for insuring compression of the material making up device 56 around needle 52. In FIGS. 11 and 13, for example, inwardly directed protrusions 82 (FIG. 11) and 84 (FIG. 13) are provided such that when split 62 is closed, a tightly sealed compression fit exists around needle 52. FIG. 12 illustrates the type of tight compression fit that should exist around needle 52 to provide the desired sealing and absorption characteristics when needle 52 is moved into and out of the puncture site.

As shown in FIGS. 14–22, sealing device 52 may include a cover or shield 86. Shield 86 includes a separation or split 88 matching the split 62 in sealing device 56. A flexible connection 90 between shield halves 92 permits the halves to close thereby closing split 62 when squeezing pressure is applied to the outside of shield 86 as shown in FIGS. 15 and 18. Further, the frangible connectors 94 between parts 58 and 60 of sealing device 56 are located on the exterior peripheries of parts 58 and 60 and between sealing device 56 and the interior wall of shield 86. Moreover, an indicator mark 96 is provided on needle 52 to establish the amount of withdrawal of needle 52 to encapsulate needle tip 64 within sealing part 58, as shown in FIG. 19.

Referring now to FIG. 14, needle 52 has been inserted into a body area 54 to puncture a vein. The sealing device 56 is placed around needle 52 and closed by a squeezing action on the outside of shield 86 as illustrated in FIGS. 15 and 18. After capturing needle 52, device 56 is pressed into engagement with the skin at the venipuncture site as shown in FIG. 15. Needle 52 is withdrawn until indicator mark 96 becomes visible at the upper end of part 58 as shown in FIG. 19, thereby insuring encapsulation of the needle tip 64 within sealing part 58. Then, needle 52 and shield 86 are withdrawn from the puncture site and frangible connectors 94 break to separate such that parts 58 and 60 separate due to the adhesive contact between part 60 and the skin at the puncture site.

Significantly, shield 86 provides an additional barrier between the doctor, nurse or technician who is extracting blood and the absorbed blood within sealing part 58. Further, shield 86 may also provide for easier manipulation of sealing device 56 for smaller needles. Moreover, shield 86 provides, in effect, a container when the needle tip 64 is encapsulated in sealing part 58 prior to disposal, as shown in FIG. 19. It will be understood by those skilled in the art that an antiviral or bacterial agent may be added to the sealing device 56 during its manufacture to provide added protection.

FIGS. 20–22 illustrate another configuration of the shielded sealing device 56. FIGS. 20 and 21 show the shield 86 having an integral and closed top and side configuration except for an opening 98 to permit movement of needle 52. The sealing part 58 for needle tip 64 is secured to the interior of shield 86 by means of an adhesive 100 or the like. Frangible connectors 102 are utilized to permit separation of parts 58 and 60 as described previously and as shown in FIGS. 20 and 21. Further, an enlarged portion of the needle 52 is provided, either in the form 104 shown in FIGS. 20 and 21, or the form 106 shown in FIG. 22, for the purpose of limiting the withdrawal of needle 52 to insure encapsulation of needle tip 64 within sealing part 58.

Figure 24:
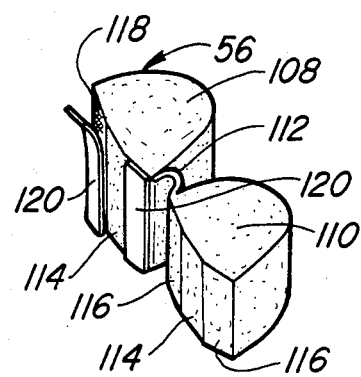
FIG. 24 is a perspective view of the sealing device shown in FIG. 23 illustrating an open position for the device.
Figure 25:
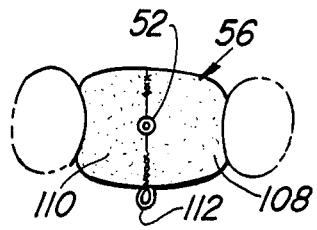
FIG. 25 is a top plan view of the sealing device shown in FIGS. 23 and 24 in a closed position around the needle.

FIGS. 23–25 illustrate yet another configuration for sealing device 56 including two portions 108 and 110 that are connected together by hinge portion 112. Each portion 108 and 110 includes a needle engaging flat surface 114 and engaging surfaces 116 that form obtuse angles with respect to surface 114. The engaging surfaces 116 of at least one of the portions 108 and 110 are coated with an adhesive 118 that is covered by strippable covers 120. Further, as before, the skin contacting end of device 56 includes an adhesive and strippable cover assembly 122. As illustrated in FIG. 25, needle 52 is captured by squeezing the two portions 108 and 110 of sealing device 56 together. The configuration of surfaces 114 and 116 is such that a tight compressive fit results around needle 52 when the portions 108 and 110 are squeezed together thereby bringing surfaces 116 together for securement by adhesive 118.

Figure 26:
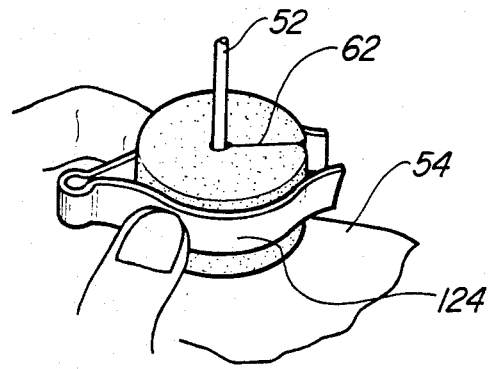
FIG. 26 is a perspective view illustrating a holding means for the sealing device.

Referring now to FIG. 26, there is illustrated yet another convenient holding means 124 for manipulating sealing device 56. As shown, holding means 124 may be utilized to squeeze the exterior of sealing device 56 for capturing needle 52 as described previously. It may be necessary to utilize holding means 124 when the needle 52 is small and short and it is difficult to place fingers directly around sealing device 56. A needle 52 of the type shown in FIG. 28, for example, may require a holding tool such as 124 to apply a squeezing action to the outside of sealing device 56 through shield 86.

Figure 27:
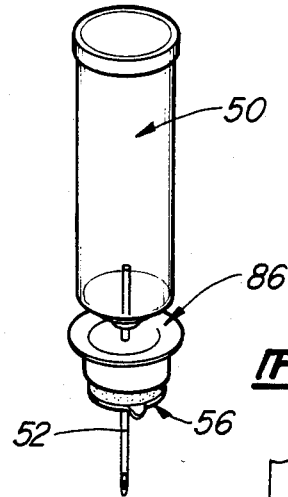
FIG. 27 is a perspective view illustrating a hypodermic unit with the sealing device of the present invention pre-mounted thereon.
Figure 28:
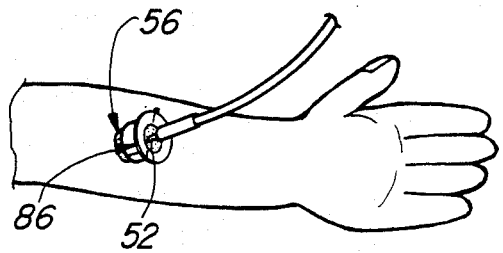
FIG. 28 is a perspective view illustrating the sealing device of the present invention as utilized with a different needle construction.
Figure 29:
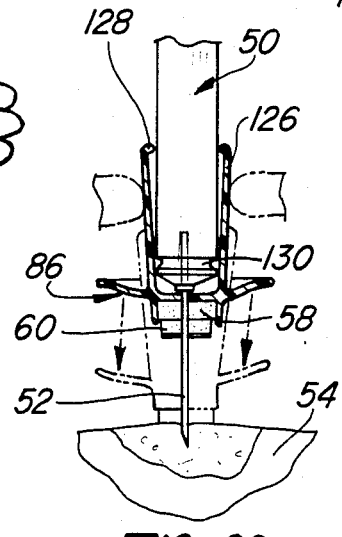
FIG. 29 is a side elevational view, partly in cross-section, illustrating another configuration for the shield around the sealing device of the present invention.
Figure 30:
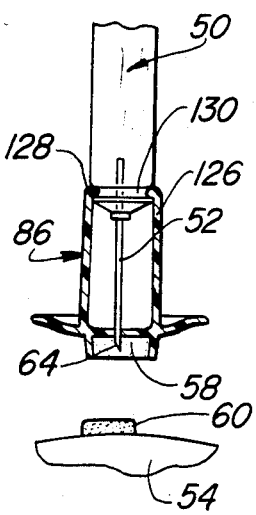
FIG. 30 is a side elevational view illustrating the operation of the assembly shown in FIG. 29.

As shown in FIGS. 27 and 28, the sealing device 56 may be pre-mounted on needle 52 so that the doctor, nurse or technician does not have to perform the above-described capturing step of the needle prior to usage. A particularly convenient configuration for the pre-mounted sealing device 56 is shown in FIGS. 29 and 30. Referring to FIG. 29, shield 86 includes an elongated resilient body portion 126 having an inwardly directed end portion 128. Initially, shield 86 and sealing device 56 are positioned at the base of needle 52. After the venipuncture is made, shield 86 is pushed downwardly for causing sealing portion 60 to contact the outer skin area around the puncture site. Needle 52 is withdrawn which detaches sealing part 60 from sealing part 58 as described previously. Shield 86 is then slid along the body of hypodermic device 50 until the inwardly directed end portion 128 of shield 86 snaps into engagement with a complementary circumferential recess 130 in device 50 as shown in FIG. 30. This automatically results in the encapsulation of needle tip 64 within sealing portion 58 thereby eliminating the need to visually watch for a mark on needle 52, as previously described, to insure the proper sealing position of needle tip 64 within sealing portion 58.

It will be obvious to those skilled in the art that various modifications can be made to the venipuncture and cutaneous sealing device and in the materials and specific configurations used therein without departing from the spirit and scope of the present invention, which is defined by the appended claims.

I claim:

1. A venipuncture and cutaneous sealing device comprising a body member of absorbent material having opposed ends and adapted for use with a needle having an end that punctures the skin of a body, said sealing device capturing said needle along its length and being movable along said needle into sealing contact with the skin at the puncture site to seal the puncture site and absorb any blood at the puncture site, and said sealing device includes two separable parts along the length of the body member, connection means between said parts such that during usage, one part remains in contact with the skin at the puncture site and the other part remains on the needle during withdrawal of the needle whereby the one part seals the puncture site and absorbs any blood at the puncture site while the other part seals the end of the needle and absorbs any blood on the needle.

2. The sealing device as defined in claim 1 wherein at least one frangible connector is provided between said separable parts.

3. The sealing device as defined in claim 1 wherein said sealing device includes a separation having opposed surfaces with the needle being captured therebetween and with the opposed surfaces forming a compression fit around the needle.

4. The sealing device as defined in claim 1 wherein one of said opposed surfaces having adhesive thereon.

5. The sealing device as defined in claim 3 wherein said opposed surfaces include inwardly directed protrusions adjacent the needle to provide a tightly sealed compression fit around the needle.

6. The sealing device as defined in claim 1 wherein adhesive is provided on the sealing device where the sealing device contacts the skin at the puncture site.

7. The sealing device as defined in claim 6 wherein means are provided to assist in the stripping of the sealing device away from the skin.

8. The sealing device as defined in claim 1 wherein an antiviral or bacterial agent is included in the sealing device.

9. The sealing device as defined in claim 1 wherein a cover is provided around the sealing device.

10. The sealing device as defined in claim 9 wherein the cover is movable and includes a resilient body having an inwardly directed end portion which is engageable with a complementary recess in a holder for the needle.

11. The sealing device as defined in claim 3 wherein a cover is provided around the sealing device, said cover having a separation matching the separation in the sealing device.

12. The sealing device as defined in claim 1 wherein means are provided on said needle to indicate when the needle end is encapsulated within said other part.

13. The sealing device as defined in claim 8 wherein means are provided on said needle for engagement with said cover to indicate when the needle end is encapsulated within said sealing device.

14. The sealing device as defined in claim 1 wherein said sealing device includes two portions that are pivotally connected together, each portion including a needle engaging surface and other surfaces that form angles with respect to said needle engaging surface, and said other surfaces of said portions being squeezed together such that a tight compressive fit results around the needle.

15. A method of sealing a puncture made by a needle having an end that punctures the skin of a body comprising the steps of:
   capturing the needle along its length;
   puncturing the skin of a body within the needle end;
   moving a sealing device along the needle into sealing contact with the skin at the puncture site; and
   removing the needle thereby leaving the sealing device to seal the puncture site and absorb any blood at the puncture site; and
   wherein the sealing device includes two separate parts and the method of sealing further includes the steps of contacting the skin at the puncture site with one of the separable parts, separating the parts during withdrawal of the needle from the puncture such that one part remains on the skin and the other part remains on the needle, sealing the puncture site with the one part and absorbing any blood at the puncture site with the one part, and sealing the end of the needle with the other part and absorbing any blood on the needle with the other part.

16. The method as defined in claim 15 wherein the sealing device includes a separation having opposed surfaces and the method of sealing further includes the steps of capturing the needle along its length between the opposed surfaces and squeezing the opposed surfaces together around the needle to form a compression fit around the needle.

17. The method as defined in claim 16 wherein a cover is provided around the sealing device and the method of sealing further includes the step of squeezing the cover around the sealing device to form the compression fit around the needle.

18. The method as defined in claim 15 wherein a cover is provided around the sealing device with the cover having an elongated resilient body and an inwardly directed end portion, and the method of sealing further includes the steps of moving the cover and sealing device along the length of the needle after puncturing the skin with the needle end such that the one part contacts the skin at the puncture site, withdrawing the needle for separating the parts, and moving the cover relative to the needle for engaging the inwardly directed end portion of the cover with a complementary recess in a holder for the needle thereby insuring encapsulation of the needle end within the other part of the sealing device.

19. In a needle device having a needle including an end that punctures the skin of a body and a holder for the needle, the improvement comprising:
   a venipuncture and cutaneous sealing device comprising a body member of absorbent material having opposed ends and adapted for use with the needle, said sealing device capturing said needle along its length and being movable along said needle into sealing contact along the length of the body member, connection means between said parts such that during usage the skin at the puncture site to seal the puncture site and absorb any blood at the puncture site, and said sealing device includes two separable parts, with one part remains in contact with the skin at the puncture site and the other part remains on the needle during withdrawal of the needle whereby the one part seals the puncture site and absorbs any blood at the puncture site while the other part seals the end of the needle and absorbs any blood on the needle.

20. The needle device as defined in claim 19 wherein at least one frangible connector is provided between said separable parts.

21. The needle device as defined in claim 19 wherein said sealing device includes a separation having opposed surfaces with the needle being captured therebetween and with the opposed surfaces forming a compression fit around the needle.

22. The needle device as defined in claim 21 wherein one of said opposed surfaces having adhesive thereon.

23. The needle device as defined in claim 19 wherein adhesive is provided on the sealing device where the sealing device contacts the skin at the puncture site.

24. The needle device as defined in claim 19 wherein a cover is provided around the sealing device.

25. The needle device as defined in claim 24 wherein the cover is movable and includes a resilient body having an inwardly directed end portion which is engageable with a complementary recess in said holder for the needle.

26. The needle device as defined in claim 19 wherein means are provided on said needle to insure that the needle end is encapsulated within the sealing device upon withdrawal of the needle from the puncture.

27. The needle device as defined in claim 24 wherein means are provided on said needle for engagement with said cover to insure that the needle end is encapsulated within said sealing device upon withdrawal of the needle from the puncture.

28. The needle device as defined in claim 19 wherein said sealing device includes two portions that are pivotally connected together with each portion including a needle engaging surface and other surfaces that form angles with respect to said needle engaging surface, and said other surfaces of said portions being squeezed together such that a tight compressive fit results around the needle.

* * * * *